United States Patent [19]

Lund

[11] Patent Number: Plant 5,279

[45] Date of Patent: Sep. 4, 1984

[54] BEGONIA PLANT

[76] Inventor: Shirley J. Lund, 906 Van Dr., Williamsburg, Iowa 52361

[21] Appl. No.: 457,271

[22] Filed: Jan. 11, 1983

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Dennison, Meserole, Pollack & Scheiner

[57] ABSTRACT

A begonia cultivar Agnes Kennison distinguishable from its parent Begonia X erythrophylla commonly referred to as Beefsteak Begonia, by the colorful pink, cream and green variegated leaves.

2 Drawing Figures

1

The present invention relates to a new and distinctive cultivar of begonia plant, known by the varietal name Agnes Kennison and classified as a rhizomatous begonia.

The new cultivar was discovered by me in my daughter's home as a color mutation of parent Begonia X erythrophylla commonly referred to as Beefsteak Begonia.

Asexual reproductin of the new cultivar by rhizome cuttings taken with leaves has reproduced the unique features of the new cultivar through successive propagations.

The principal characteristic distinguishing the new begonia from its parent is the colorful variegation of the leaves. Each leaf is marked differently. Some are patterned with random areas of pink, cream and one or more shades of green. As an example of their variances, some leaves appear as though they had been splashed with pink on a green leaf with a paint brush. Occasionally a leaf will be half pink and half green or green splashed with cream and even all pink.

The new variety Agnes Kennison has been cultivated by me in my home in Williamsburg, Iowa.

The accompanying photographs show the different colored leaves of a typical specimen of my new cultivar of begonia plant, the coloring of which is shown as nearly true as possible in a color reproduction of this type.

The following is a detailed description of my new begonia cultivar based on plants grown at Williamsburg. Color references are made to The Royal Horticultural Society (R.H.S.) Colour Chart 1, issued by Wilson Colour Ltd. in collaboration with The Royal Horticultural Society and a Dictionary of Color (ADC), Second Edition, A. Maerz and M. R. Paul, McGraw-Hill Book Company, Inc., 1950.

Parentage: Color Mutation of parent Begonia X erythrophylla.

Propagation: By rhizome cuttings taken with leaves.

Rooting habit: The rhizome piece along with a few leaves is all that is necessary and if some roots are retained on the pieces of rhizome when propagating, the cuttings start putting new leaves sooner than if rootless rhizome pieces are used.

Foliage: Leaves are alternate, ovate-rounded to almost circular, broadly obtuse to very shortly acute, deeply cordate at the base with rounded basal lobes often

2 overlapping, and with slightly sinuate, obscurely and remotely dentate, ciliate margin. Veins underneath the leaves are abundantly fine-hairy; the upper surface is glabrous except for the ciliate margin. Some of the mature, thick and coriaceous leaves reach 8 inches to 8½ inches across. Rather large keeled, ovate-acute, long-ciliate and setose-tipped, persistent stipules remain on the thick, repent to ascending rhizome and eventually become dry, brownish and papery. Petioles, as long as or longer than the leave, are pole green and sparsely red hairy. Fibrous roots from the rhizome are pink and gray.

Foliage color: New foliage is near light scarlet, R.H.S. 19/3; underside nearly rose madder, R.H.S. 23/1. However, specimens with only one color pink near light crimson, R.H.S. 22/2 or ADC Plate L 8F Pink Pearl; underside deeper, near R.H.S. 22. More mature foliage varies between ADC Plate 10 2C cream nearly ivory, and carmine rose, R.H.S. 621/2, fading into tranparent over green, but varies to rose madder, R.H.S. 19/1. More mature single-color leaves are nearly pale carmine rose, R.H.S. 621/3; underside, scarlet, R.H.S. 19/1. Green of foliage is dull shade nearest to emerald green, R.H.S. 758 or ADC Plate 24 12A Brunswick green.

Blooming season: In winter and spring.

Blooming habits: Large, one-sided cymes, on peduncles which rise above the glossy, leathery leaves.

Flowers: Masses of small 2-tepaled, deep-pink flowers are borne in large, one-sided cymes on 14 inch to 16 inch tall, erect, pink, sparsely red-hairy peduncles, which rise above the glossy, leathery leaves. Bracts are hairy.

Disease resistance: No diseases noted.

Growth conditions: The new cultivar is vigorous and hardy to 45° F., which it tolerates without damage. The leaves benefit from indoor lighting, but direct sunlight is beneficial for foliage coloration.

I claim:

1. A new and distinct cultivar of begonia plant known by the cultivar name Agnes Kennison and particularly characterized as to hardiness and uniqueness of leaf coloration and color pattern, with the leaves being variegated patterned with random areas of pink, cream and one or more shades of green.

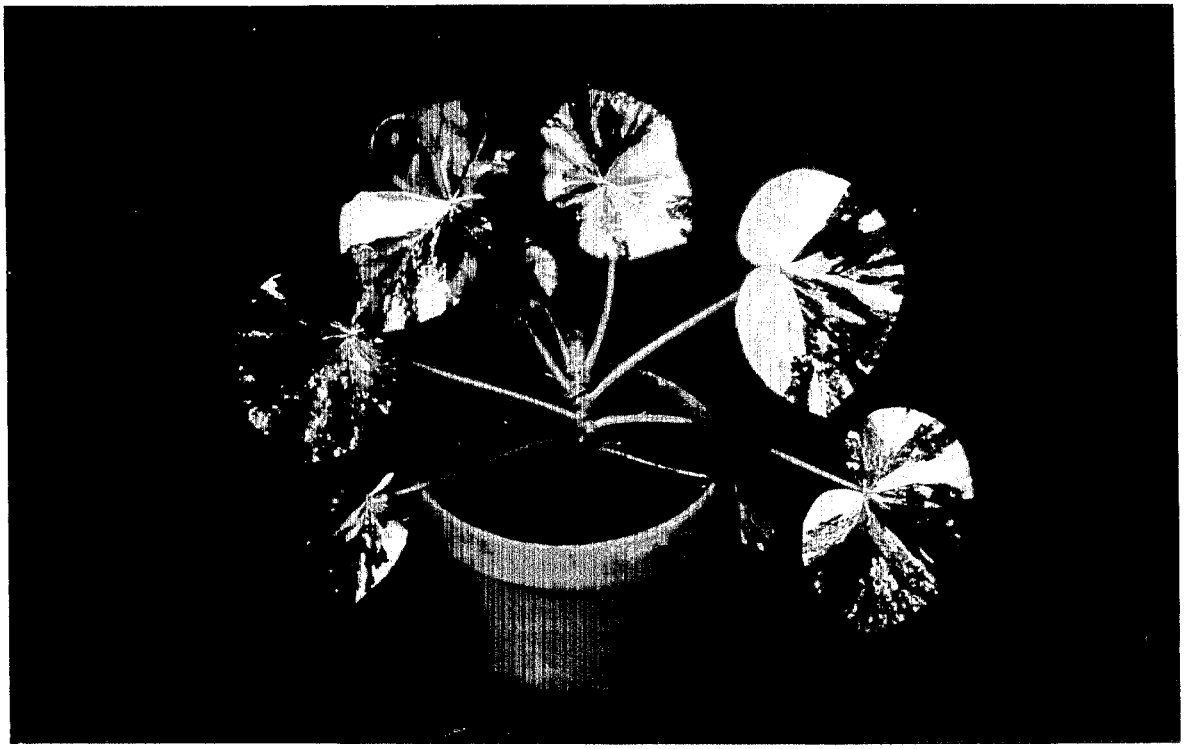
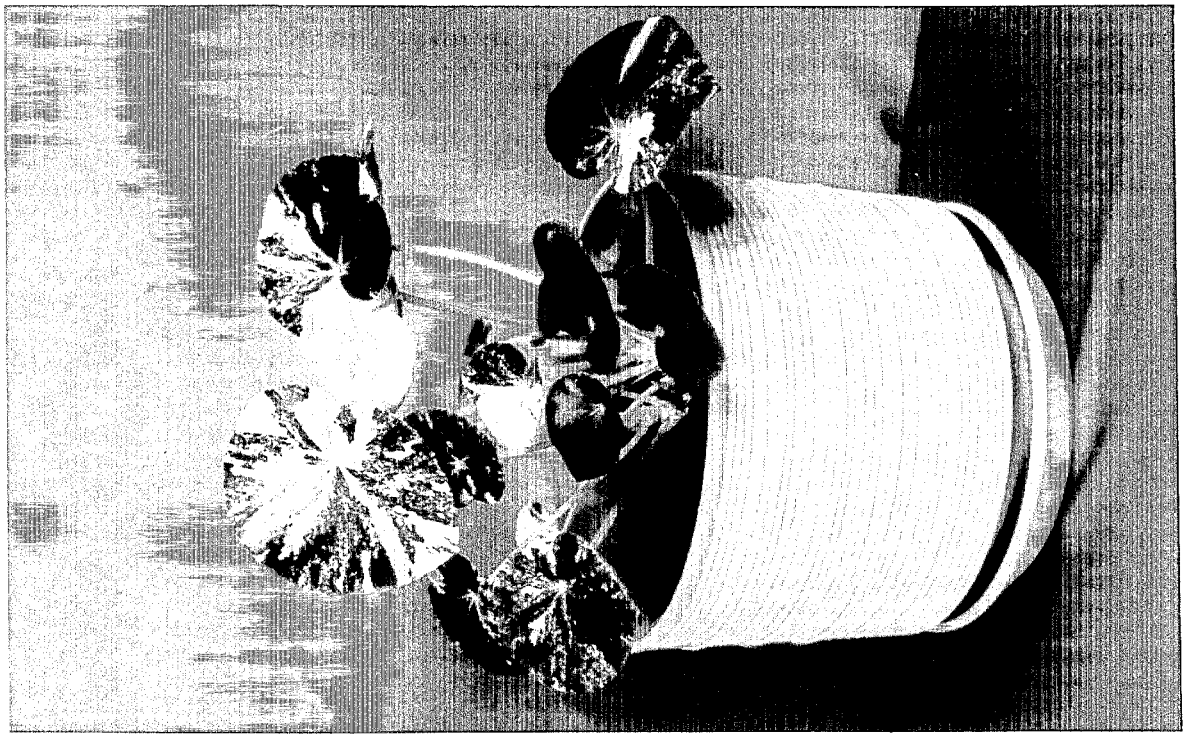

* * * * *